(12) United States Patent
Gershon et al.

(10) Patent No.: US 10,682,295 B2
(45) Date of Patent: Jun. 16, 2020

(54) CONTROLLING ZINC OXIDE PARTICLE SIZE FOR SUNSCREEN APPLICATIONS

(71) Applicant: International Business Machines Corporation, Armonk, NY (US)

(72) Inventors: Talia S. Gershon, White Plains, NY (US); Ning Li, Yorktown Heights, NY (US); Devendra Sadana, Yorktown Heights, NY (US); Teodor K. Todorov, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/449,182

(22) Filed: Mar. 3, 2017

(65) Prior Publication Data

US 2017/0172862 A1      Jun. 22, 2017

Related U.S. Application Data

(62) Division of application No. 15/082,676, filed on Mar. 28, 2016.

(60) Provisional application No. 62/213,668, filed on Sep. 3, 2015.

(51) Int. Cl.

| A61K 8/11 | (2006.01) |
|---|---|
| A61K 8/27 | (2006.01) |
| A61Q 17/04 | (2006.01) |
| A61K 8/25 | (2006.01) |
| A61K 8/92 | (2006.01) |
| A61K 8/02 | (2006.01) |

(52) U.S. Cl.
CPC .............. *A61K 8/11* (2013.01); *A61K 8/0241* (2013.01); *A61K 8/0275* (2013.01); *A61K 8/25* (2013.01); *A61K 8/27* (2013.01); *A61K 8/922* (2013.01); *A61Q 17/04* (2013.01); *A61K 2800/26* (2013.01); *A61K 2800/262* (2013.01); *A61K 2800/413* (2013.01); *A61K 2800/621* (2013.01); *A61K 2800/651* (2013.01)

(58) Field of Classification Search
None
See application file for complete search history.

(56) References Cited

U.S. PATENT DOCUMENTS

| 3,761,261 A | 9/1973 | Ono et al. |
|---|---|---|
| 3,863,007 A | 1/1975 | Warner, Jr. |
| 4,549,195 A | 10/1985 | Bluzer |
| 5,011,782 A | 4/1991 | Lamb |
| 5,028,417 A | 7/1991 | Bhat et al. |
| 5,030,699 A | 7/1991 | Hendrickson |
| 5,147,125 A | 9/1992 | Austin |
| 5,223,250 A | 6/1993 | Mitchell |
| 5,441,726 A | 8/1995 | Mitchnick |
| 5,534,056 A | 7/1996 | Kuehnle |
| 5,553,630 A | 9/1996 | Dupuis et al. |
| 5,902,569 A | 5/1999 | Oshima |
| 6,419,909 B1 | 7/2002 | Lorant |
| 6,534,044 B1* | 3/2003 | Wada ................... A61K 8/0212 106/436 |
| 6,599,355 B1* | 7/2003 | Schmidt ................... C08K 9/02 106/415 |
| 7,143,805 B1 | 12/2006 | Weir |
| 7,241,399 B2 | 7/2007 | Haubold |
| 7,514,863 B2 | 4/2009 | Lee |
| 8,647,373 B1 | 2/2014 | Shepherd |
| 9,056,063 B2 | 6/2015 | Hanson |
| 9,144,535 B1 | 9/2015 | Daly et al. |
| 9,144,536 B1 | 9/2015 | Daly et al. |
| 9,773,931 B2 | 9/2017 | Hossain |
| 9,883,993 B2* | 2/2018 | Gershon ................... A61K 8/29 |
| 9,889,074 B2* | 2/2018 | Gershon ................... A61K 8/29 |
| 2002/0122832 A1 | 9/2002 | Hanke |
| 2003/0102099 A1 | 6/2003 | Yadav |
| 2004/0209081 A1 | 10/2004 | Hagihara |
| 2005/0008861 A1 | 1/2005 | Yadav et al. |
| 2005/0048010 A1 | 3/2005 | Kliss |
| 2005/0208005 A1 | 9/2005 | Giroud |
| 2005/0227063 A1 | 10/2005 | Lawandy |
| 2005/0238600 A1 | 10/2005 | Lien |

(Continued)

FOREIGN PATENT DOCUMENTS

| CN | 103071535 A | 5/2013 |
|---|---|---|
| CN | 104609459 A | 5/2015 |

(Continued)

OTHER PUBLICATIONS

Smijs et al. Titanium Dioxide and Zinc Oxide Nanoparticles in Sunscreens: Focus on Their Safety and Effectiveness, Nanotechnology, Science and Applications 4:95-112, Oct. 2011.

Wikipedia, List of Refractive Indices, last modified Feb. 15, 2017; https://en.wikipedia.org/wiki/List_of_refractive_indices.

Thokozane Moses Sithole, Synthesis and characterization of MBxOy:Eu (M=Ca, Sr, Ba) phosphors and TiO2 semiconductor for application in luminescence and energy materials, University of the Free State, Nov. 2014.

Sardar et al., Optical-absorption intensities and intermanifold emission cross sections of trivalent erbium ions in calcium fluorophosphate, Journal of Applied Physics, Sep. 2005.

(Continued)

*Primary Examiner* — Katherine Peebles
(74) *Attorney, Agent, or Firm* — Ryan, Mason & Lewis, LLP

(57) ABSTRACT

Zinc oxide compositions and methods for controlling zinc oxide particle size for sunscreen applications are provided herein. An example composition includes multiple zinc oxide particles, wherein each of the zinc oxide particles is (i) coated with an optical coating material and (ii) of a size that is below a maximum threshold; and a medium layer within which the zinc oxide particles are suspended, wherein the medium layer comprises a mixture of one or more media, and wherein each of the media has a refractive index below a predetermined threshold.

1 Claim, 2 Drawing Sheets

(56) References Cited

U.S. PATENT DOCUMENTS

| | | |
|---|---|---|
| 2005/0265935 A1 | 12/2005 | Hollingsworth |
| 2006/0228310 A1 | 10/2006 | Lyth |
| 2006/0241211 A1 | 10/2006 | Coughlin |
| 2006/0270053 A1 | 11/2006 | Tilak |
| 2007/0280895 A1 | 12/2007 | Weimer |
| 2008/0107695 A1 | 5/2008 | Fleissman |
| 2008/0149850 A1 | 6/2008 | Tardif et al. |
| 2008/0181920 A1* | 7/2008 | Buerger .................. A61K 8/27 424/401 |
| 2008/0220026 A1 | 9/2008 | Maltra |
| 2009/0022765 A1 | 1/2009 | Chung et al. |
| 2009/0061001 A1 | 3/2009 | Hougaz |
| 2009/0104130 A1 | 4/2009 | Bernstein |
| 2009/0258072 A1 | 10/2009 | Schlossman |
| 2009/0258230 A1 | 10/2009 | Schlossman |
| 2010/0008872 A1 | 1/2010 | Katusic |
| 2010/0040567 A1* | 2/2010 | Katusic .................. A61K 8/25 424/59 |
| 2010/0055138 A1 | 3/2010 | Margulies |
| 2010/0310871 A1 | 12/2010 | McCormick |
| 2011/0268678 A1 | 11/2011 | Armstrong |
| 2013/0006118 A1 | 1/2013 | Pan |
| 2013/0039858 A1 | 2/2013 | Brown |
| 2013/0216834 A1 | 8/2013 | Hashimoto |
| 2014/0142213 A1 | 5/2014 | Weiss |
| 2014/0242129 A1 | 8/2014 | Gaurav |
| 2015/0283059 A1 | 10/2015 | Nagare |
| 2016/0082513 A1 | 3/2016 | Niedermeyer |

FOREIGN PATENT DOCUMENTS

| | | |
|---|---|---|
| EP | 1889810 A1 | 2/2008 |
| JP | 39059591 A | 3/1997 |
| JP | 2008024677 A | 2/2008 |
| JP | 2011102291 A | 5/2011 |
| WO | 2005023535 A2 | 3/2005 |
| WO | 2008017176 A2 | 2/2008 |
| WO | 2008079758 A1 | 7/2008 |
| WO | 2011004133 A2 | 1/2011 |
| WO | 2011089571 A2 | 7/2011 |
| WO | 2012046204 A1 | 4/2012 |
| WO | 2013040149 | 3/2013 |
| WO | 2013094639 A1 | 6/2013 |
| WO | 2014040177 A1 | 3/2014 |
| WO | 2014049139 A1 | 4/2014 |
| WO | 2014077189 | 5/2014 |
| WO | 2016020168 A1 | 2/2016 |

OTHER PUBLICATIONS

Lu et al., 2008—White Up-Conversion Luminescence in Rare-Earth-Ion-Doped YAlO3 Nanocrystals, J. Phys. Chem. C 2008, 112, 15071-15074.

Refractive index of ZnO (Zinc oxide)—Bond-o, http://refractiveindex.info/?shelf=main&book=ZnO&page=Bond-o, Mar. 25, 2016.

Refractive index of SiO2 (Silicon dioxide, Silica, Quartz)—Malitson, http://refractiveindex.info/?shelf=main&book=SiO2&page=Malitson, Mar. 25, 2016.

Schubert et al., Design of multilayer antireflection coatings made from co-sputtered and low-refractive-index materials by genetic algorithm. Optics Express vol. 16, No. 8, 2008.

Law et al., ZnO—Al2O3 and ZnO—TiO2 Core-Shell Nanowire Dye-Sensitized Solar Cells. J. Phys. Chem. B 2006, 110, 22652-22663.

Pu et al., Core/shell structured ZnO/SiO2 nanoparticles: Preparation, characterization and photocatalytic property. Applied Surface Science 257 (2010) 393-397.

Mantz et al., Progress in Organic Coatings 47 (2003) 432-442, "A multiple-scattering model analysis of zinc oxide pigment for spacecraft thermal control coatings."

Song et al., Toxicology Letters 199 (2010) 389-397, "Role of the dissolved zinc io and reactive oxygen species in cytotoxicity of ZnO nanoparticles."

Bohren et al., "Absorption and Scattering of Light by Small Particles", Wiley-VCH, © 2004, Weinheim.

Bae et al., J. Phys. Chem. B 2005, 109, 2526-2531, "Comparative Structure and Optical Properties of Ga-, In-, and Sn-Doped ZnO Nanowires Synthesized by thermal evaporation."

NanoComposix, Silver Nanoparticles: Optical Properties, http://nanocomposix.com/pages/silver-nanoparticles-optical-properties, Apr. 20, 2016.

Awazu et al., 2007—A Plasmonic Photocatalyst Consisting of Silver Nanoparticles Embedded in Titanium Dioxide, J. Am. Chem. Soc. 2008, 130, 1676-1680.

Sherry et al., Localized Surface Plasmon Resonance Spectroscopy of Single Silver Nanocubes, Nano Lett., vol. 5, No. 10, 2005.

Aguirre et al., Ag@ZnO Core_Shell Nanoparticles Formed by the Timely Reduction of Ag+ Ions and Zinc Acetate Hydrolysis in N,N-Dimethylformamide: Mechanism of Growth and Photocatalytic Properties, J. Phys. Chem. C 2011, 115, 24967-24974.

Haynes et al., Nanosphere Lithography: Tunable Localized Surface Plasmon Resonance Spectra of Silver Nanoparticles, J. Phys. Chem. B 2000, 104, 10549-10556.

U. Nobbmann, "FAQ: How important are refractive index & adsorption for nanoparticles?" http://www.materials-talks.com/blog/2014/08/05/faq-how-important-are-refractive-index-absorption-for-nanoparticles/ Materials Talks, Aug. 5, 2014, p. 1-2.

Tsuzuki et al., Nanoparticle Coatings for UV Protective Textiles, RJTA vol. 14 No. 2 2010.

Li et al., Transparent and Light-Emitting Epoxy Super-Nanocomposites Containing ZnO-QDs/SiO2 Nanocomposite Particles as Encapsulating Materials for Solid-State Lighting, J. Phys. Chem. C 2008, 112, 18616-18622.

Li et al., 2011—Sol-gel preparation and characterization of nanoporous ZnO_SiO2 coatings with broadband antireflection properties, Applied Surface Science 257 (2011) 9752-9756.

Messaoudi et al., "Synthesis and characterization of ZnO/Cu2O core-shell nanowires grown by two-step electrodeposition method." Applied Surface Science 343 (2015) 148-152.

Luo et al., Facile synthesis of composition-tuned ZnO/ZnxCd1-xSe nanowires for photovoltaic applications, Nanoscale Research Letters (2015) 10:181.

Naylor et al. "Sunscreens," accessed 2017, http://telemedicine.org/sundam/sundam2.4.2.html.

Ultraviolet Radiation and the Intersun Programme [online]. WHO, Nov. 2003 [retrieved on Jun. 8, 2017]. Retrieved from the internet <http://www.who.int/uv/uv_and_health/en/>.

Machine translation WO 2011/004133, printed 2017.

Wikipedia "Band Gap" last modified Jul. 18, 2017, https://en.wikipedia.org/wiki/Band_gap.

Machine translation WO 2012/046204, printed 2017.

Faure, B. et al. Dispersion and Surface Functionalization of Oxide Nanoparticles for Transparent Photocatalytic and UV-protecting Coatings and Sunscreens, Sci Technol. Adv. Mater. 14 2013, 023001.

Tariq Jan, et al. Sn Doping Induced Enhancement in the Activity of ZnO Nanostructures Against Antibiotic Resistant S. aureus Bacteria; Int J. Nanomedicine, vol. 8, pp. 3679-3687; Published online Sep. 30, 2013.

Bhatti et al. Optical Properties of Chromium & Cobalt Doped Zinc Oxide Powder Prepared by Sol-Gel Combustion Method, with the Assistance of Microwave Radiations; International Journal of Advanced Tech. in Engineering and Science; vol. 3, Issue 10; pp. 80-85; published Oct. 2015.

Cuprous Oxide, Chemical Book, pp. 1-4, Accessed Sep. 18, 2017, https://www.chemicalbook.com/ProductChemicalPropertiesCB9853041_EN.htm.

Family Health Team, "Best Ways to Protect Your Hair From Sun Damage," Cleveland Clinic, health essentials, <https://health.clevelandclinic.org/2014/08/best-ways-to-protect-your-hair-from-sun-damage/>, published Aug. 22, 2014, p. 1-4.

Simon Aldridge and Anthony Downs. The Group 13 Metals Aluminum, Gallium, Indium and Thallium Chemical Patterns and Peculiarities, 2011 John Wiley & Sons, Ltd., p. 623 (Year: 2011).

Machine translation, JP 2008-024677, printer 2018.

(56) References Cited

OTHER PUBLICATIONS

Kelly et al. "The Optical Properties of Metal Nanoparticles: The Influence of Size, Shape and Dielectric Environment," Journal of Physical Chemistry B 107:668-677, 2003.
Garcia, "Surface Plasmons in Metallic Nanoparticles: Fundamentals and Applications," Journal of Physics D: Applied Physics 44(28), 283001, 2011.
Latha et al. "Sunscreening Agents: A Review," Journal of Clinical and Aesthetic Dermatology 6(1):16-26, 2013.
Sreejith et al. "Squaraine Dyes: A Mine of Molecular Materials," Journal of Materials Chemistry 18:264-274, 2008.
Merriam-Webster "Roughen." Merriam-Webster.com, Merriam-Webster, n.d. Web. Aug. 22, 2018 (Year: 2018).
English language translation of WO 2013094639 (A1) (Year: 2013).

\* cited by examiner

CONTROLLING ZINC OXIDE PARTICLE SIZE FOR SUNSCREEN APPLICATIONS

FIELD

The present application generally relates to chemical technology, and, more particularly, to sunscreen technologies.

BACKGROUND

Sunscreen creams and other such compositions are commonly used to prevent ultraviolet (UV) radiation (also referred to herein as "light" in this context) from reaching the skin of a human user and causing damage. It is noted that UV light is an electromagnetic radiation with a wavelength range between approximately 280 nanometers (nm) and approximately 400 nanometers (specifically, that is the range of UV radiation that is not absorbed by the ozone).

A common active ingredient of existing sunscreen compositions is zinc oxide (ZnO). ZnO is a semiconductor that has a specific band gap, and particles of ZnO used in existing sunscreen compositions are typically approximately 50-200 nm in size. Additionally, in existing sunscreen compositions, typical ZnO materials are capable of absorbing UV light (that is, blocking the UV light from passing through the sunscreen composition to be absorbed by the skin of the user) within a wavelength range of approximately 290 nm through only approximately 350-380 nm.

Additionally, high sun protection factor (SPF) sunscreen compositions, which can absorb a large majority of the UV light in the range of 290-380 nm, require the addition of a higher density of ZnO particles, which causes the composition to become white and/or opaque due to light scattering from the ZnO particles, and which is an often undesirable property to consumers.

SUMMARY

In one embodiment of the present invention, zinc oxide compositions and methods for controlling zinc oxide particle size for sunscreen applications are provided. An exemplary method can include steps of manipulating the size of multiple zinc oxide particles to be below a predetermined maximum threshold; selecting one or more media, from a collection of multiple media, to be used in a sunscreen composition, wherein said selecting is based on the refractive index of each of the multiple media; and integrating the multiple manipulated zinc oxide particles into the one or more selected media to create the sunscreen composition.

In another embodiment of the invention, a composition can include multiple zinc oxide particles, wherein each of the multiple zinc oxide particles is (i) coated with an optical coating material and (ii) of a size that is below a predetermined maximum threshold; and a medium layer within which the multiple zinc oxide particles are suspended, wherein the medium layer comprises a mixture of one or more media, and wherein each of the one or more media has a refractive index below a predetermined threshold.

These and other objects, features and advantages of the present invention will become apparent from the following detailed description of illustrative embodiments thereof, which is to be read in connection with the accompanying drawings.

DETAILED DESCRIPTION

As described herein, an embodiment of the present invention includes zinc oxide compositions, methods of fabrications thereof and methods of use thereof. Specifically, at least one embodiment of the invention includes controlling ZnO particle size for sunscreen applications. Additionally, at least one embodiment of the invention includes controlling the amount of scattering in connection with use of a sunscreen composition by controlling the size of ZnO particles in the sunscreen composition. As used herein, "scattering" refers to the deflection of rays of visible light from their original path due to interaction with particle surfaces.

As further detailed herein, one or more embodiments of the invention include generating ZnO compositions and methods of use thereof for effectively blocking more and/or all of the complete spectrum of UV light (that is, as noted above, the UV radiation that is not absorbed by the ozone, and which ranges between approximately 280 nm and 400 nm) while also preventing whitening effects caused by the scattering of light in the visible spectrum (that is, radiation between approximately 400 nm and 700 nm).

At least one embodiment of the invention includes reducing particle size for ZnO particles in a sunscreen composition to a size of less than 100 nm, such as, for example between 30 nm and 80 nm. By way of example, at least one embodiment of the invention includes manipulating the size of ZnO particles to dimensions smaller than the wavelength(s) of visible light in order to decrease scattering of visible light, as particle scattering coefficients decrease as the particle size of ZnO decreases.

Additionally, as further detailed in connection with FIG. 1, one or more embodiments of the invention can include aggregating multiple ZnO particles into clusters, for example, to prevent penetration through skin, and thereby improve product safety. Such clusters, by way of example, can be of a size that is greater than 200 nm. Such aggregation can be carried out, for example, and as further detailed in connection with FIG. 2, by introducing a binding agent or anchoring particle that functions to bring together ZnO nanoparticle clusters. Such binding agent introduction is carried out in a manner that minimizes total scattering from the cluster of particles.

Also, and as further detailed in connection with FIG. 3 and FIG. 4, one or more embodiments of the invention can include selecting a particular sunscreen (lotion) medium based on the refractive index of the medium, and/or modifying the refractive index of a particular sunscreen medium via integration of one or more additional media. By way of example, at least one embodiment of the invention includes utilizing a sunscreen medium having a refractive index that is between that of ZnO and that of (ambient) air.

Figure 1:
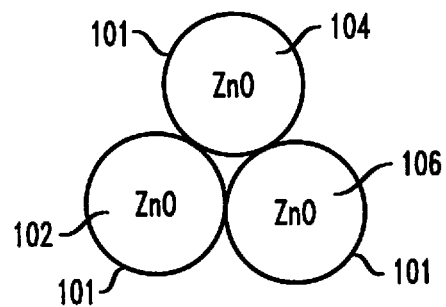
FIG. 1 is a diagram illustrating a configuration of ZnO particles, according to an exemplary embodiment of the invention.

FIG. 1 is a diagram illustrating a configuration of ZnO particles, according to an exemplary embodiment of the invention. By way of illustration, FIG. 1 depicts aggregating ZnO particles 102, 104 and 106 that are coated with a coating material 101 or enveloped within a shell, which results in the aggregated particles to remain optically separate. In one or more embodiments of the invention, the coating or shell material 101 can have a refractive index that is in between that of ZnO and that of air. One example of such a material can include silicon dioxide ($SiO_2$). By controlling the thickness of the coating or shell, the refractive index of the coating or shell, and the refractive index of the sunscreen (lotion) medium, the scattering of visible light by the aggregate of ZnO particles (which can cause undesirable whitening of the sunscreen (lotion)) can be minimized. In the absence of such a coating or shell, and in the absence of measures to control the given optical properties, the aggregates of ZnO particles might scatter light in a manner similar to that of one larger particle.

Figure 2:
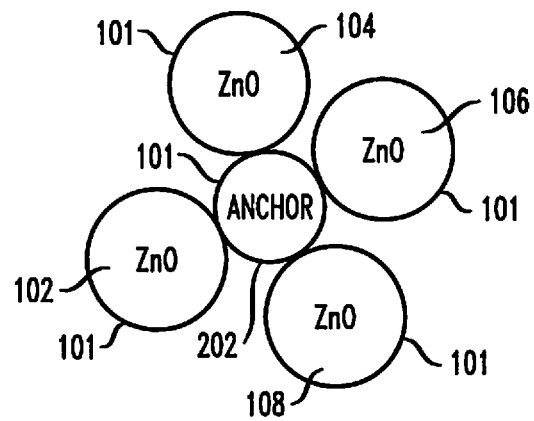
FIG. 2 is a diagram illustrating a configuration of ZnO particles, according to an exemplary embodiment of the invention.

FIG. 2 is a diagram illustrating a configuration of ZnO particles, according to an exemplary embodiment of the invention. By way of illustration, FIG. 2 depicts an anchoring particle 202 (also referred to herein as a binding agent) that is utilized to aid the aggregation of ZnO particles 102, 104, 106 and 108. By way of example, another ZnO particle can be used as such an anchoring particle, wherein the anchoring particle's surface is modified such that the anchoring particle can bind to other particles. Similarly to the configuration depicted in FIG. 2, this illustrated configuration utilizes the anchoring particle 202, in part, to ensure that the aggregated particles remain optically separate.

Figure 3:
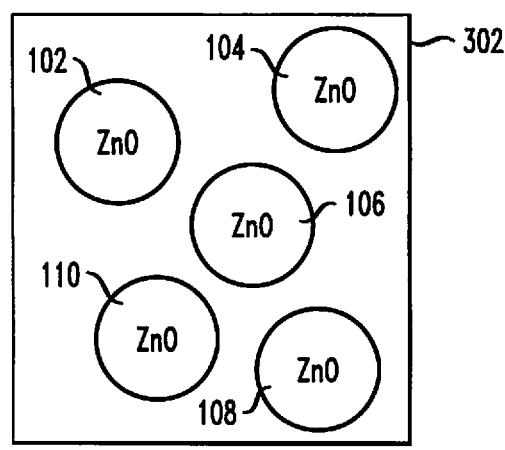
FIG. 3 is a diagram illustrating a configuration of ZnO particles in conjunction with at least one sunscreen medium, according to an exemplary embodiment of the invention.
Figure 4:
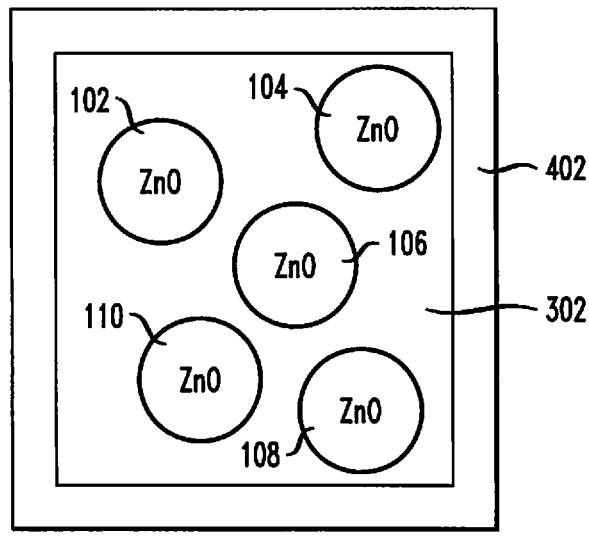
FIG. 4 is a diagram illustrating a configuration of ZnO particles in conjunction with at least one sunscreen medium, according to an exemplary embodiment of the invention.
Figure 5:
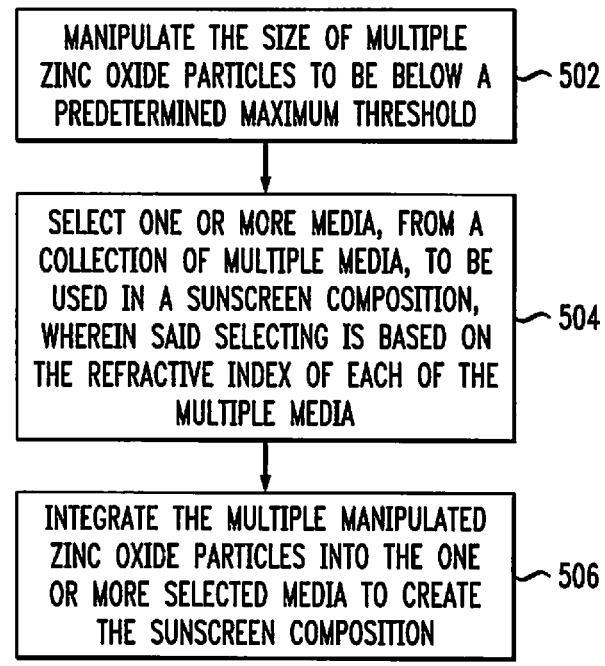
FIG. 5 is a flow diagram illustrating techniques, according to an embodiment of the invention.

FIG. 3 is a diagram illustrating a configuration of ZnO particles in conjunction with at least one sunscreen medium, according to an exemplary embodiment of the invention. By way of illustration, FIG. 3 depicts ZnO particles 102, 104, 106, 108 and 110 positioned and/or integrated within a sunscreen lotion medium 302. As further detailed herein, the particular lotion medium 302 can be selected as one or more media on the basis of refractive index to minimize scattering from the ZnO particles.

Accordingly, one or more embodiments of the invention include reducing scattering from ZnO particles by embedding ZnO particles in a sunscreen (lotion) medium with an appropriate refractive index (n). By way of illustration, consider a scenario wherein $n_{air} < n_{lotion} < n_{ZnO}$. In such a scenario, $n_{lotion}$ can be selected as a sunscreen medium to minimize scattering.

It is noted that the refractive index of ZnO is approximately 1.9-2.1 (λ-dependent), while common media and their corresponding refractive index can include the following: water (n~1.35), coconut oil (n~1.44), mineral oil (n~1.46), and polyparabens (n~1.50). One or more embodiments of the invention can include combining and/or mixing two or more media in a particular ratio that optimizes optical properties (for example, a target refractive index).

FIG. 4 is a diagram illustrating a configuration of ZnO particles in conjunction with at least one sunscreen medium, according to an exemplary embodiment of the invention. By way of illustration, FIG. 4 depicts ZnO particles 102, 104, 106, 108 and 110 positioned and/or integrated within sunscreen lotion medium 302. Additionally, FIG. 4 depicts a second layer of a lotion medium 402 that is applied on top of medium 302. In one or more embodiments of the invention, the second layer of lotion medium 402 (the top layer) can include a medium having a smaller refractive index than lotion medium 302 (the bottom layer) containing the ZnO particles. In one or more embodiments of the invention, a configuration such as depicted in FIG. 4 can additionally be modified and/or designed to further minimize the scattering of visible light by the ZnO particles. Similarly, the example embodiments illustrated herein are merely non-limiting examples, and it is to be appreciated that additional components and embodiments can be implemented. For example, additional oils (such as, for example, shea butter) can be utilized as a medium in one or more embodiments of the invention.

FIG. 5 is a flow diagram illustrating techniques according to an embodiment of the present invention. Step 502 includes manipulating the size of multiple zinc oxide particles to be below a predetermined maximum threshold. The predetermined maximum threshold can include, for example, 100 nanometers. Additionally, in one or more embodiments of the invention, manipulating can include manipulating the size of multiple zinc oxide particles to be (i) below a predetermined maximum threshold and (ii) above a predetermined minimum threshold. In such an embodiment, the predetermined maximum threshold can include 80 nanometers, and the predetermined minimum threshold can include 30 nanometers.

Step 504 includes selecting one or more media, from a collection of multiple media, to be used in a sunscreen composition, wherein said selecting is based on the refractive index of each of the multiple media. Selecting one or more media based on refractive index can include selecting one or more media having a refractive index between 1 and 2.

Step 506 includes integrating the multiple manipulated zinc oxide particles into the one or more selected media to create the sunscreen composition. In one or more embodiments of the invention, selecting one or more media can include selecting (i) a first medium having a first refractive index and (ii) a second medium having a second refractive index. In such an embodiment, the integrating step can include integrating the multiple manipulated zinc oxide particles into the first medium, and applying the second medium on top of the first medium, wherein the second refractive index is smaller than the first refractive index.

The techniques depicted in FIG. 5 can also include aggregating one or more subsets of the multiple zinc oxide particles into one or more clusters, wherein the one or more clusters each be of a size of greater than 200 nanometers. One or more embodiments of the invention can additionally include applying an optical coating (such as, for example, $SiO_2$) to each of the multiple zinc oxide particles in each of the one or more clusters to create an optical separation between each of the multiple zinc oxide particles in each of the one or more clusters. Also, in at least one embodiment of the invention, aggregating can include using one or more binding agents, wherein the binding agents can include one or more nanospheres and/or one or more particles of a substance which may include zinc oxide.

Additionally, the techniques depicted in FIG. 5 can also include combining two or more media from the collection of multiple media in a determined ratio to create a target refractive index.

Also, an additional embodiment of the invention includes a composition that include multiple zinc oxide particles, wherein each of the multiple zinc oxide particles is (i) coated with an optical coating material and (ii) of a size that is below a predetermined maximum threshold (for example, 100 nm), and a medium layer within which the multiple zinc oxide particles are suspended, wherein the medium layer comprises a mixture of one or more media, and wherein each of the one or more media has a refractive index below a predetermined threshold (for example, a refractive index of 2). In one or more embodiments of the invention, the optical coating material can include silicon dioxide.

Such a composition can also include a second medium layer applied on top of the medium layer within which the multiple zinc oxide particles are suspended, wherein the second medium layer has a refractive index that is smaller than the refractive index of the medium layer within which the multiple zinc oxide particles are suspended. Additionally, in one or more such embodiments, the mixture of one or more media can include a mixture of two or more media in a determined ratio to create a target refractive index. Further, in one or more such embodiments, the multiple zinc oxide particles can be aggregated into one or more clusters, and the one or more clusters can also include one or more binding agents.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of another feature, step, operation, element, component, and/or group thereof.

At least one embodiment of the present invention may provide a beneficial effect such as, for example, controlling the amount of scattering in connection with use of a sunscreen composition by controlling the size of ZnO particles in the sunscreen composition.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A composition consisting of:

multiple zinc oxide particles aggregated into one or more clusters, wherein each of the multiple zinc oxide particles is (i) coated with silicon dioxide of a user-controlled thickness based on a desired reduction of scattering of visible light by the multiple zinc oxide particles and (ii) of a size that is below a predetermined maximum threshold of 80 nanometers and above a predetermined minimum threshold of 30 nanometers, wherein the one or more clusters each is a size of greater than 200 nanometers, wherein each of the one or more clusters comprises the multiple silicon dioxide-coated zinc oxide particles bound to a respective anchoring particle, wherein the anchoring particle comprises a zinc oxide particle having a modified surface, wherein the modified surface of each respective anchoring particle physically contacts the optical coating of each of the silicon dioxide-coated zinc oxide particles within the respective cluster via direct modified surface of anchoring particle-to-silicon dioxide contact, and wherein the silicon dioxide-coated zinc oxide particles bound to the respective anchoring particle are optically separate from one another;

and a media layer consisting of water, coconut oil, mineral oil, polyparabens, and shea butter.

* * * * *